(12) United States Patent
Kitaoka et al.

(10) Patent No.: US 6,425,889 B1
(45) Date of Patent: Jul. 30, 2002

(54) DISPOSABLE DIAPER

(75) Inventors: Hideaki Kitaoka; Norio Nanba, both of Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/433,588

(22) Filed: Nov. 5, 1999

(30) Foreign Application Priority Data

Nov. 5, 1998 (JP) .......................................... 10-316346

(51) Int. Cl.[7] ................................................. A61F 13/15
(52) U.S. Cl. ............................. 604/385.01; 604/385.19; 604/369; 604/385.101; 604/385.29; 604/385.2
(58) Field of Search ........................ 604/385.01, 385.19, 604/369

(56) References Cited

U.S. PATENT DOCUMENTS

| | | | |
|---|---|---|---|
| 5,531,730 A | * | 7/1996 | Dreier ................. 604/385.101 |
| 5,558,660 A | | 9/1996 | Dreier |
| 5,649,918 A | | 7/1997 | Schleinz |
| 5,795,347 A | | 8/1998 | Roe et al. |
| 5,938,652 A | * | 8/1999 | Sauer ..................... 604/385.02 |
| 6,280,426 B1 | * | 8/2001 | Turner ................... 604/385.01 |

FOREIGN PATENT DOCUMENTS

| | | |
|---|---|---|
| JP | 5-15934 | 3/1993 |
| WO | WO97/48359 | 12/1997 |

* cited by examiner

*Primary Examiner*—John J. Calvert
*Assistant Examiner*—Angela J Grayson
(74) *Attorney, Agent, or Firm*—Lowe Hauptman Gilman & Berner, LLP

(57) ABSTRACT

A disposable diaper including a topsheet, and a topsheet is covered, at least in one of front and rear waist regions, with a liquid-resistant sheet bonded to a longitudinal end and transversely opposite side edges of that one of the front and rear waist regions; an elastic foamed member which is folded in two along a folding axis zone extending longitudinally thereof and has a first portion placed against the upper surface of the topsheet and a second portion placed against the lower surface of a liquid-resistant sheet is disposed between the topsheet and the liquid-resistant sheet in such a manner that the foamed member lies on an upper portion of a core in that one of the front and rear waist regions.

15 Claims, 4 Drawing Sheets

DISPOSABLE DIAPER

BACKGROUND OF THE INVENTION

This invention relates to a disposable diaper for absorption and containment of body wastes and the like.

Japanese Utility Model Application Disclosure Gazette (Kokai) No. Hei5-15934 discloses a disposable diaper comprising a topsheet, a backsheet and a liquid-absorbent core disposed between these two sheets. An upper surface of the topsheet in front and rear waist regions of the diaper is covered with exudation-proof sheets each bonded along its peripheral edge except its inner edge to the topsheet by a sealing line. The exudation-proof sheets are not bonded to the upper surface of the topsheet along its inner edges so that body wastes may flow into spaces defined between the topsheet and the exudation-proof sheets and then be absorbed by an absorbent core covered with the topsheet therethrough.

However, the above-mentioned known diaper is inconvenient in that one or both of the spaces defined between the topsheet and the exudation-proof sheets may be almost permanently closed as the topsheet and the exudation-proof sheets are forced in contact with each other under pressure of a wearer's belly and/or back. Even after such pressure has been removed, the spaces can not be opened again because there is no means biasing the spaces to be opened again. Consequently, once an amount of body wastes have reached the front and rear waist regions, such amount of body wastes may at least partially flow over the outer surface of the exudation-proof sheets and leak outward.

SUMMARY OF THE INVENTION

In view of the problem as has been described above, it is an object of the present invention to provide an improved disposable diaper enabling it to prevent body wastes from leaking outward from front and rear waist regions of a diaper.

According to the present invention, there is provided a disposable diaper comprising a liquid-pervious topsheet, a liquid-impervious backsheet and a liquid-absorbent core disposed between the topsheet and the backsheet to form a front waist region, a rear waist region and a crotch region extending between the front and rear waist regions in a longitudinal direction orthogonal to a transverse direction of the diaper, the topsheet being covered, at least in one of the front and rear waist regions, with a liquid-resistant sheet bonded to a longitudinal end and transversely opposite side edges of the one of the front and rear waist regions; an elastic foamed member which is folded in two along a folding axis zone extending longitudinally thereof and has a first portion placed against an upper surface of the topsheet and a second portion placed against a lower surface of the liquid-resistant sheet being disposed between the topsheet and the liquid-resistant sheet in such a manner that the foamed member lies on an upper portion of the absorbent core in the one of the front and rear waist regions with the folding axis zone being held in the vicinity of the longitudinal end of the one of the front and rear waist regions; and the first and second portions cooperating with each other to form a pocket opening toward the crotch region and one of the first and second portions extends toward the crotch region over a distance longer than that over which the other extends toward the crotch region.

According to one embodiment of the present invention, a distance over which the second portion extends toward the crotch region is in a range of 25~35 mm and a distance over which the first portion extends toward the crotch region is in a range of 5~10 mm.

According to another embodiment of the present invention, a distance over which the first portion extends toward the crotch region is in a range of 25~35 mm and a distance over which the second portion extends toward the crotch region is in a range of 5~10 mm.

According to the present invention, said foamed member can be formed selectively by polyurethane foam, synthetic rubber foam or polystyrene foam so far as all of them being of soft type.

DETAILED DESCRIPTION OF THE PREFERRED EMBODIMENTS

Details of a disposable diaper according to the present invention will be more fully understood from the description given hereunder with reference to the accompanying drawings.

Figure 1:
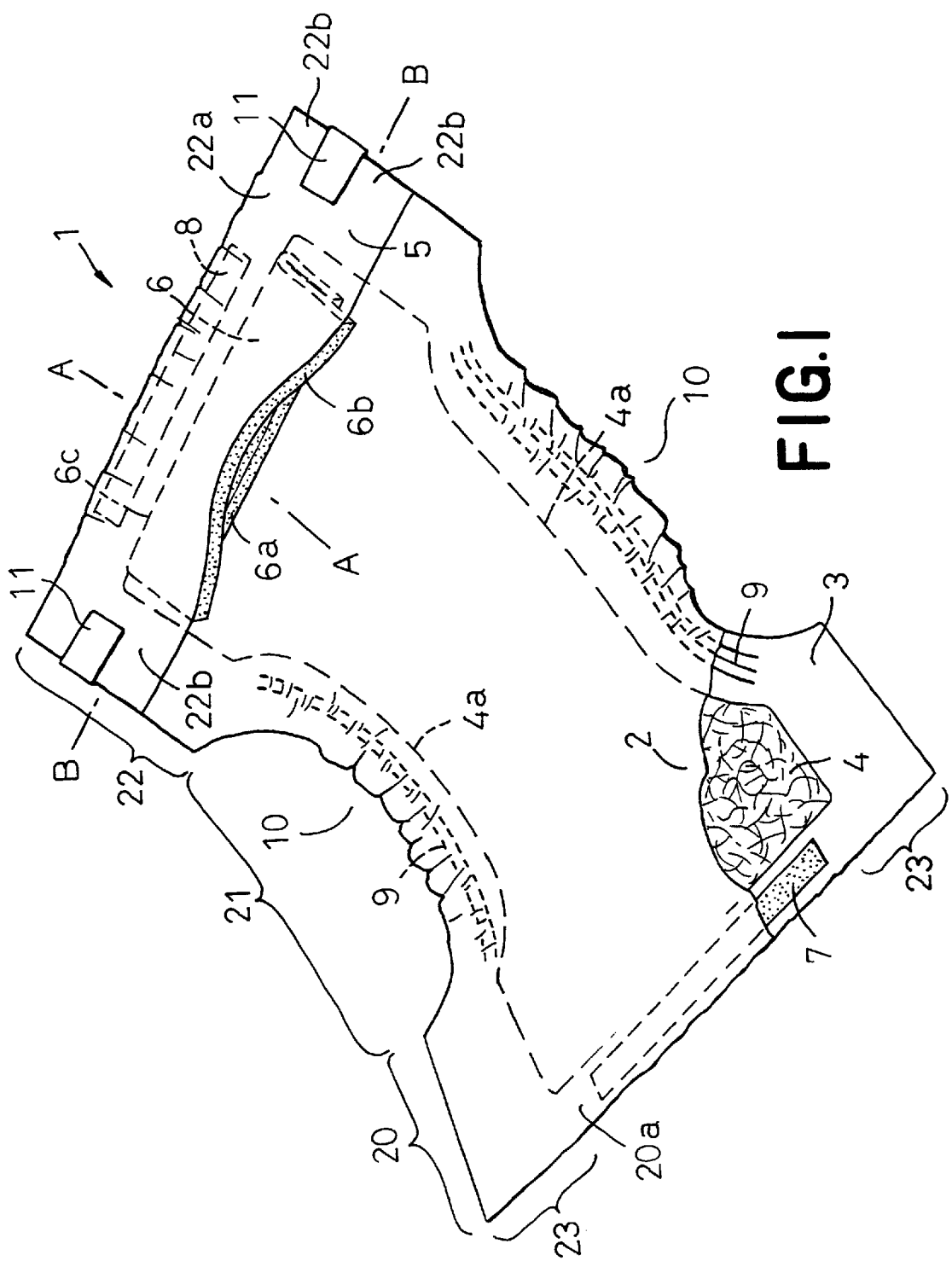
FIG. 1 is a perspective view showing a partially cutaway disposable diaper according to one embodiment of the present invention.
Figure 2:
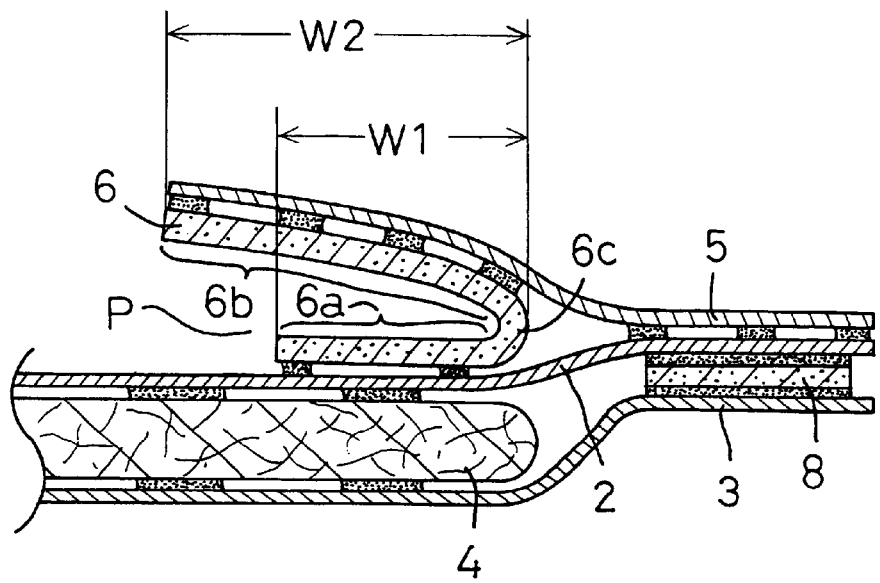
FIG. 2 is a sectional view taken along a line A—A in FIG. 1.

FIG. 1 is a perspective view showing a partially cutaway diaper 1 according to one embodiment of the present invention and FIG. 2 is a sectional view taken along a line A—A in FIG. 1. The diaper 1 comprises a liquid-pervious topsheet 2, a liquid-impervious backsheet 3 and an hourglass-shaped liquid-absorbent core 4 disposed between the topsheet 2 and the backsheet 3 and bonded to inner surfaces of these two sheets 2, 3. Configurationally, the diaper 1 is composed of a front waist region 20, a rear waist region 22 and a crotch region 21 as viewed in a longitudinal direction which is orthogonal to a transverse direction of the diaper 1.

In the rear waist region 22 of the diaper 1, the topsheet 2 is partially covered with a liquid-resistant sheet 5 having a width larger than a width of the core 4. The liquid-resistant sheet 5 is bonded to the upper surface of the topsheet 2 at a longitudinally outer edge 22a and transversely opposite side edges 22b of the rear waist region 22.

An elastically deformable rectangular foamed member 6 is folded in two along a folding axis zone 6c extending longitudinally of the foamed member 6 and disposed between the topsheet 2 and the liquid-resistant sheet 5. The foamed member 6 disposed therebetween in this manner lies on an upper portion of the core 4 in the rear waist region 22 with the folding axis zone 6c lying adjacent the longitudinally upper edge 22a of the rear waist region 22.

The foamed member 6 comprises a first portion 6a placed against the upper surface of the topsheet 2 and a second portion 6b overlying the first portion 6a in contact with the lower surface of the liquid-resistant sheet 5. The first portion 6a has its lower surface bonded to the upper surface of the topsheet 2 and the second portion 6b has its upper surface bonded to the lower surface of the liquid-resistant sheet 5.

The first and second portions 6a, 6b cooperate with each other to form a pocket P opening toward the crotch region 21.

Referring to FIG. 2, the foamed member 6 is dimensioned so that a distance, i.e., a width W2 over which the second portion 6b extends from the folding axis zone 6c toward the crotch region 21 is larger than a distance, i.e., a width W1 over which the first portion 6a extends from the folding axis zone 6c toward the crotch region 21. Preferably, the foamed member 6 is dimensioned so that the width W2 of the second portion 6b is in a range of 25~35 mm and the width W1 of the first portion 6a is in a range of 5~10 mm.

The diaper 1 is formed with a pair of side flaps 23 extending outward from transversely opposite side edges 4a, 4a of the core 4. The side edges 4a are formed with cutouts 10, 10 which are concavely curved inward transversely of the diaper 1. Along the respective cutouts 10, elastic members 9 destined to surround respective legs of a diaper wearer are disposed between the topsheet 2 and the backsheet 3 and secured under tension to the inner surface of at least one of these two sheets 2, 3.

Along longitudinally opposite ends 20a, 22a of the diaper 1, i.e., along respective longitudinally outer ends of the front and rear waist regions 20, 22, film-shaped elastic members 7, 8 are disposed between the topsheet 2 and the backsheet 3 and bonded to the inner surfaces of these two sheets 2, 3 so that these elastic members 7, 8 circumferentially extend around the wearer's waist. The rear waist region 22 is provided with a pair of tape fasteners 11 respectively extending from its transversely opposite side edges 22b outward transversely of the diaper 1. The tape fasteners 11 are folded inward transversely of the diaper 1 and provisionally anchored to the upper surface of the liquid-resistant sheet 5.

Figure 3:
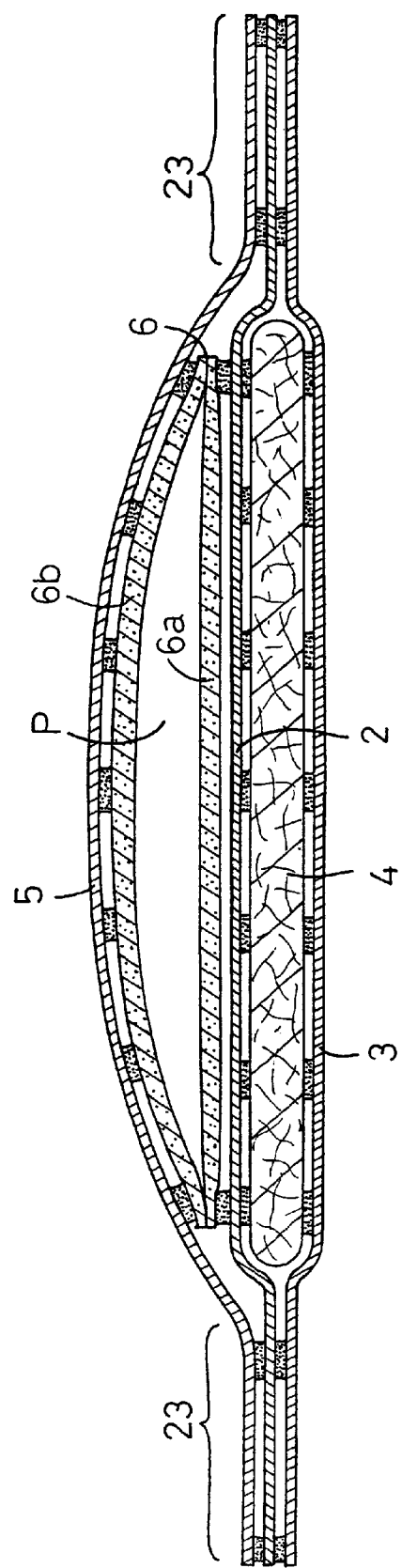
FIG. 3 is a sectional view taken along a line B—B in FIG. 1.

FIG. 3 is a sectional view taken along a line B—B in FIG. 1. While the pocket P is collapsed and closed under pressure exerted thereon by the wearer's back, the first and second portions 6a, 6b of the foamed member 6 is elastically biased to moved away from each other as the pressure is removed or alleviated. Consequently, the second portion 6b is elastically pivoted upward around the folding axis zone 6c and spaced above from the topsheet 2. In this manner, the pocket P is opened again.

In the diaper 1 according to this embodiment, the width of the first portion 6a over which this covers the topsheet 2 is relatively small and allows a correspondingly larger area of the topsheet 2 to be exposed. An amount of body wastes directly flowing into the pocket P is absorbed by the core 4 through the topsheet 2. On the other hand, an amount of body wastes having reached the first portion 6a is absorbed once by the foamed member 6, but it is forced to exude therefrom as the pocket P is collapsed under pressure of the wearer's back and absorbed by the core 4 through the topsheet 2. The liquid-resistant sheet 5 overlying the second portion 6b of the foamed member 6 functions to prevent the body wastes from exuding outward.

Figure 5:
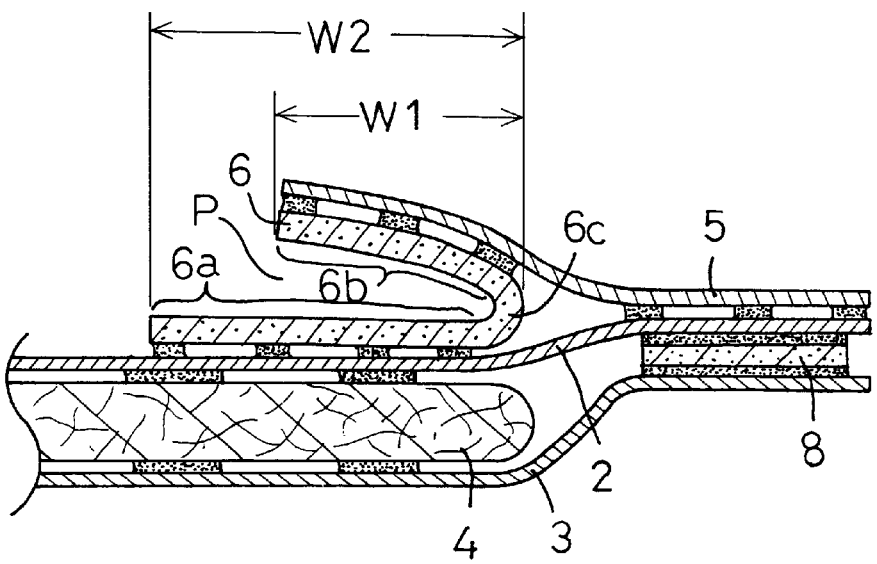
FIG. 5 is a sectional view taken along a line C—C in FIG. 4.
Figure 4:
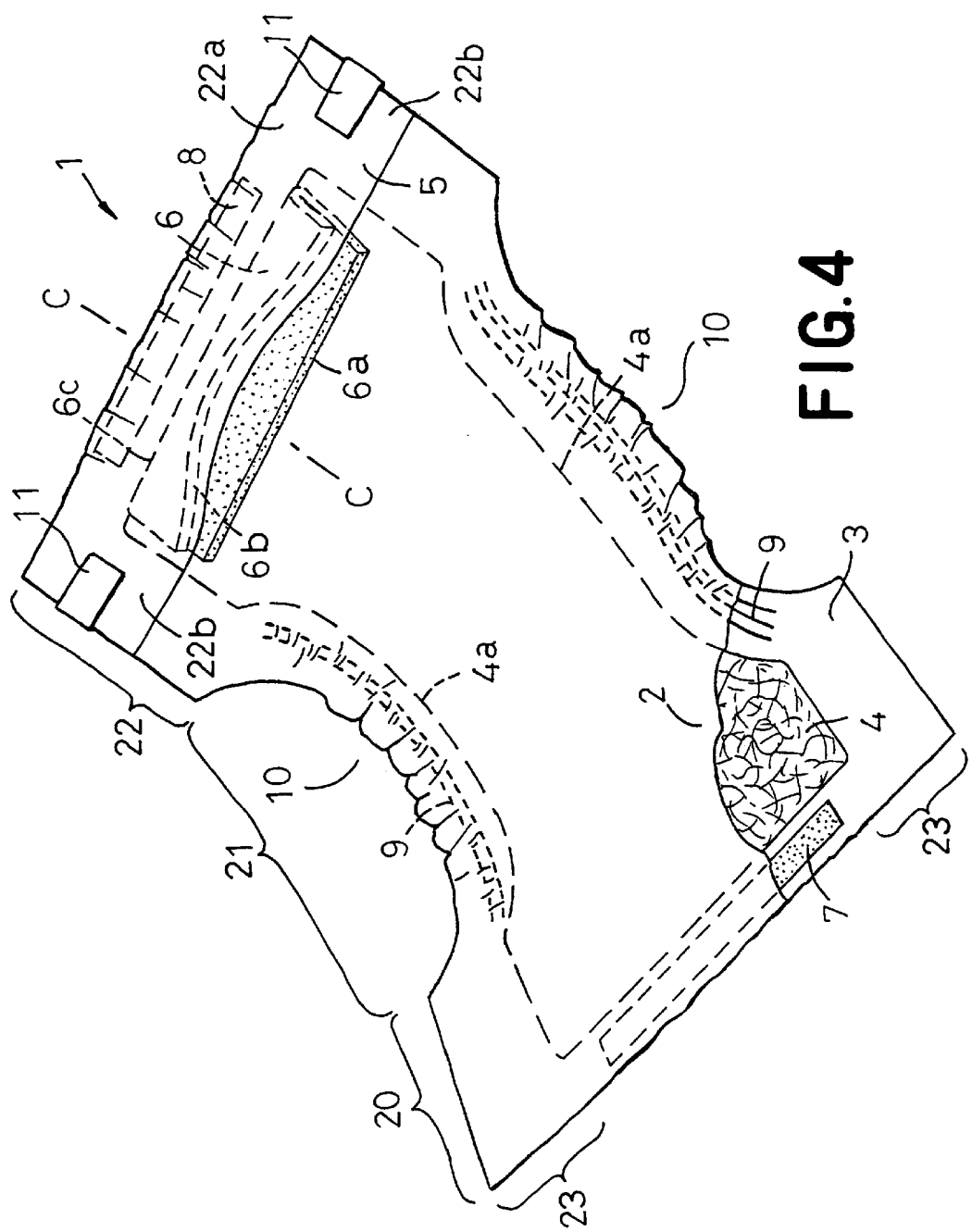
FIG. 4 is a view similar to FIG. 1 showing a disposable diaper according to another embodiment of the present invention.

FIG. 4 is a perspective view showing the diaper 1 according to an embodiment different from the embodiment shown in FIG. 1 and FIG. 5 is a sectional view taken along a line C—C in FIG. 4. The foamed member 6 is folded in two along the folding axis zone 6c extending longitudinally of the foamed member 6 and disposed between the topsheet 2 in the rear waist region 22 and the liquid-resistant sheet 5 so that the foamed member 6 lies on the upper portion of the core 4 in the rear waist region 22 with the folding axis zone 6c lying adjacent the longitudinally upper edge of the rear waist region 22.

The foamed member 6 comprises the first portion 6a placed against the upper surface of the topsheet 2 and the second portion 6b overlying the first portion 6a in contact with the lower surface of the liquid-resistant sheet 5. The first portion 6a has its lower surface bonded to the upper surface of the topsheet 2 and the second portion 6b has its upper surface bonded to the lower surface of the liquid-resistant sheet 5. The first and second portions 6a, 6b cooperate with each other to form the pocket P opening toward the crotch region 21.

Referring now to FIG. 5, the foamed member 6 is dimensioned so that a width over which the first portion 6a extends from the folding axis zone 6c toward the crotch region 21 is larger than a width over which the second portion 6b extends from the folding axis zone 6c toward the crotch region 21. Preferably, the foamed member 6 is dimensioned so that the width of the first portion 6a is in a range of 25~35 mm and the width of the second portion 6b is in a range of 5~10 mm.

In the case of this diaper 1, the second portion 6b dimensioned to be relatively narrow is not easily collapsed due to its increased weight when it absorbs an amount of body wastes. Even after collapsed under pressure of the wearer's back, the second portion 6b readily pivotes around the folding axis zone 6c upward to its initial position above the first portion 6a as soon as the pressure is removed.

Stock material for the foamed member 6 may be selected from a group consisting of urethane foam, synthetic rubber foam and polystyrene foam so far as they are of soft-type. While they may be open cell foam or closed cell foam, it is preferred to use the open cell foam in view of a desired breathability.

It is possible without departing from the scope of the present invention to bond the foam member 6 along its folding axis zone 6c to at least one of the upper surface of the topsheet 2 and the lower surface of the liquid-resistant sheet 5. Furthermore, it is also possible to bond at least one of the lower surface of the first portion 6a and the upper surface of the second portion 6b to one of the upper surface of the topsheet 2 and the lower surface of the liquid-resistant sheet 5.

The term "liquid-resistant sheet 5" should be understood to mean a breathable or non-breathable and liquid-impervious or liquid permeation retardant sheet. Stock material for the liquid-resistant sheet 5 may be selected from a group consisting of a plastic film, a finely porous plastic film, a nonwoven fabric of hydrophobic fibers having a high density, and the like. Concerning the liquid-resistant sheet 5, it is possible without departing from the scope of the present invention to fold its portion extending outward from the longitudinal end of the diaper 1 onto the lower surface of the backsheet 3 and then to bond this portion to the backsheet 3.

As stock material for the topsheet 2, a hydrophilic nonwoven fabric obtained by treating a hydrophobic nonwoven fabric treated with suitable hydrophilicizer or rubbing such hydrophilicizer into fibers may be used. It is also possible to realize such a nonwoven fabric in the form of finely porous nonwoven fabric.

The backsheet 3 may be formed by a synthetic resin film, laminated sheet consisting of a synthetic resin film and a hydrophobic nonwoven fabric, or the like. The core 4 may be formed by mixing fluff pulp with superabsorptive polymer particles, then pressing this mixture to a desired thickness and completely covering this with a liquid-pervious sheet.

The present invention may be realized in such a manner that the topsheet 2 is covered with the liquid-resistant sheet 5 in both the front and rear waist regions 20, 22 and the foamed members 6 are disposed between these two sheets 2, 5 so as to form the pockets P not only in the rear waist region 22 but also in the front waist region 20.

With the disposable diaper according to the present invention, the pocket formed by the first and second portions of the foamed member is elastically biased to move away from each other so that the pocket having been collapsed under pressure exerted thereon by the wearer's back is opened again as soon as the pressure is removed. In this manner, undesirable leakage of body wastes can be reliably prevented.

The first and second portions of the foamed member are dimensioned to extend toward the crotch region so as to define a difference in level between forward ends of the first and second portions. In this manner, a thickness of the foamed member the wearer feels can be alleviated sufficiently to avoid that the thickness of the foamed member might affect a feeling to wear the diaper. In addition, use of the soft foamed member improves a cushioning property thereof contributing to a good feeling to wear the diaper.

What is claimed is:

1. A disposable diaper, comprising
   a basic diaper structure comprising a liquid-pervious topsheet, a liquid-impervious backsheet and a liquid absorbent core disposed between said topsheet and said backsheet, said basic diaper structure having a front waist region, a rear waist region and a crotch region extending between the front and rear waist regions in a longitudinal direction orthogonal to a transverse direction of the basic diaper structure;
   a liquid-resistant sheet partially covering said topsheet at least in one of said front and rear waist regions, said liquid-resistant sheet bonded to said basic diaper structure to form, between said liquid-resistant sheet and said topsheet, a first pocket open toward said crotch region; and
   an elastic member placed in the first pocket, said elastic member being folded along a folding line that divides said elastic member into a first portion placed against an upper surface of said topsheet and a second portion placed against a lower surface of said liquid-resistant sheet, said first and second portions cooperating with each other to form a second pocket opening toward said crotch region and biasing said liquid-resistant sheet away from said topsheet.

2. The diaper according to claim 1, wherein a distance over which said second portion extends from the folding line toward the crotch region is in a range of from about 25 to about 35 mm, and a distance over which said first portion extends from the folding line toward the crotch region is in a range of from about 5 to about 10 mm.

3. The diaper according to claim 1, wherein a distance over which said first portion extends from the folding line toward the crotch region is in a range of from about 25 to about 35 mm, and a distance over which said second portion extends from the folding line toward the crotch region is in a range of from about 5 to about 10 mm.

4. The diaper according to claim 1, wherein said elastic member is formed of a soft foam material including at least one of polyurethane foam, synthetic rubber foam or polystyrene foam.

5. The diaper according to claim 1, wherein said liquid-resistant sheet is bonded to transversely opposite side edges of said basic diaper structure in said one of the front and rear waist regions.

6. The diaper according to claim 5, wherein said liquid-resistant sheet is further bonded to a longitudinal end of said basic diaper structure that is associated with said one of the front and rear waist regions.

7. The diaper according to claim 5, wherein said liquid-resistant sheet is folded over a longitudinal end of said basic diaper structure that is associated with said one of the front and rear waist regions, and is further bonded to a lower surface of said backsheet.

8. The diaper according to claim 1, wherein said first portion of said elastic member spans over said absorbent core in said one of the front and rear waist regions.

9. The diaper according to claim 1, wherein the folding line of said elastic member is bonded to at least one of the upper surface of said topsheet and the lower surface of said liquid-resistant sheet.

10. The diaper according to claim 1, wherein one of said first and second portions extends from the folding line toward said crotch region over a distance longer than that of the other.

11. The diaper according to claim 1, wherein said first and second portions of said elastic member are bonded to the upper surface of said topsheet and the lower surface of said liquid-resistant sheet, respectively.

12. The diaper according to claim 1, wherein said liquid-resistant sheet has a width as measured in the transverse direction of said basic diaper structure larger than that of said absorbent core.

13. The diaper according to claim 1, wherein said elastic member is made of a foam material.

14. The diaper according to claim 13, wherein the foam material is of an open cell foam type.

15. The diaper according to claim 1, wherein said elastic member is made of an absorbent material for absorbing body liquids.

* * * * *